US010429329B2

(12) United States Patent
Stacey et al.

(10) Patent No.: US 10,429,329 B2
(45) Date of Patent: Oct. 1, 2019

(54) ENVIRONMENTAL SENSOR TEST METHODOLOGY

(71) Applicant: AMS SENSORS UK LIMITED, Cambridge (GB)

(72) Inventors: Simon Jonathan Stacey, Ely (GB); Kaspars Ledins, Cambridge (GB); Matthew Govett, Cambridge (GB)

(73) Assignee: AMS SENSORS UK LIMITED, Cambridge (GB)

( * ) Notice: Subject to any disclaimer, the term of this patent is extended or adjusted under 35 U.S.C. 154(b) by 448 days.

(21) Appl. No.: 15/010,152

(22) Filed: Jan. 29, 2016

(65) Prior Publication Data

US 2017/0219506 A1 Aug. 3, 2017

(51) Int. Cl.
G01N 27/12 (2006.01)
G01N 33/00 (2006.01)

(52) U.S. Cl.
CPC ........... *G01N 27/12* (2013.01); *G01N 33/007* (2013.01); *G01N 27/124* (2013.01)

(58) Field of Classification Search
CPC ....... G01N 27/12; G01D 18/00; G01D 18/008
USPC .......................................................... 73/1.06
See application file for complete search history.

(56) References Cited

U.S. PATENT DOCUMENTS

| | | | |
|---|---|---|---|
| 5,659,125 A | 8/1997 | Ernst | |
| 6,287,878 B1 * | 9/2001 | Maeng et al. | H01L 22/20 257/E21.525 |
| 7,781,877 B2 * | 8/2010 | Jiang et al. | H01L 21/561 257/686 |
| 8,689,604 B2 * | 4/2014 | Schultz et al. | G01D 18/008 702/108 |
| 9,618,569 B2 * | 4/2017 | Benjamin et al. | G01R 31/2874 |
| 2002/0168772 A1 | 11/2002 | Lloyd et al. | |
| 2003/0015768 A1 * | 1/2003 | Bosco et al. | G02B 6/12004 257/528 |
| 2006/0131495 A1 | 6/2006 | Logsdon et al. | |
| 2010/0148814 A1 * | 6/2010 | Yalei et al. | G01R 31/2891 324/750.22 |
| 2013/0296658 A1 * | 11/2013 | Souriau et al. | B81B 7/007 600/300 |

(Continued)

OTHER PUBLICATIONS

Author: Mitsuhiro Nakamura, Title: Testing at Earliest Stages in Development Can Help Lower Costs of Microelectromechnaical Systems, Date: Jun. 6, 2008, Publication: On-Wafer Evaluation of MEMS Devices by robottf, pages total: 10.*

(Continued)

*Primary Examiner* — Paul M. West
(74) *Attorney, Agent, or Firm* — Tucker Ellis LLP

(57) ABSTRACT

We disclose herein a method for testing a batch of environmental sensors to determine the fitness for purpose of the batch of environmental sensors, the method comprising: performing a plurality of electrical test sequences to the sensor inputs of the batch of environmental sensors to measure electrical responses of the sensor outputs of the batch of environmental sensors; correlating the measured electrical responses from the batch of environmental sensors to predetermined environmental parametric ranges of at least one environmental sensor so as to define correlated electrical test limits; and determining the fitness for purpose of the batch of environmental sensors if the measured electrical responses are within the correlated electrical test limits.

40 Claims, 3 Drawing Sheets

(56) References Cited

U.S. PATENT DOCUMENTS

2013/0305804 A1    11/2013  Burchard et al.
2016/0103082 A1*    4/2016  Kimura ................ G01N 33/005
                                                                73/25.01
2016/0377569 A1*   12/2016  Rajaraman et al. .........................
                                                                G01N 27/223
                                                                257/416

OTHER PUBLICATIONS

Authors: R.Vemal, Calvin Lo, Sherrill Ong, B.S. Lee, C.C. Yong, Title: MEMS vs. IC Manufacturing: Is Integration Between Processes Possible, Date: 2009, Publisher: IEEE, 1st Int'l Symposium on Quality Electronic Design-Asia, Pages total: 5.*

Author: Ali Dianat, Title: A Resonant Based Test Methodology for Capacitive MEMs, Date: Jul. 11, 2015, Publisher: University of Windsor, Scholarship at UWindsor, Pages total: 87.*

International Search Report and Written Opinion from counterpart International Patent Application No. PCT/GB2017/050154, dated Mar. 22, 2017, pp. 13.

* cited by examiner

ENVIRONMENTAL SENSOR TEST METHODOLOGY

FIELD OF THE INVENTION

This invention relates to a method for testing a batch of environmental sensors and to an environmental sensor test system.

BACKGROUND OF THE INVENTION

Screening of environmental sensors traditionally requires running devices through a series of tests which involve exposure to environmental conditions. For example, for gas sensors, the tests involve exposure to analyte gases. This testing can take a number of hours, consumes gas and relies on specialist test equipment and chambers as well as manual handling or specialist handling equipment so is not suited to high volume and/or low cost production.

Currently the only techniques are to use extensive gas testing to screen gas sensor product. These make use of specialist test equipment that is not easily and cost effectively scaled to support high volume production. The other option is to use a golden sample reference sensor test solution which still involves the delivery of analyte gas to the test system.

Similarly, other environmental sensors such as humidity sensors and/or pressure sensors also require running the devices in the relevant environmental conditions and therefore these sensors also have the same problems as discussed above in respect of gas sensors.

SUMMARY

Embodiments of the invention apply tailored electrical test techniques to an environmental sensor product without the need for lengthy and costly product performance testing. Embodiments of the invention also apply the technique of wafer film frame handling to strips of packaged parts which has previously required specialist strip test equipment. The additional benefit of the use of a film frame is that the parts can be easily electrically isolated by cutting any linking metal conductors using a sawing process.

According to one aspect of the present invention, there is provided a method for testing a batch of environmental sensors to determine the fitness for purpose of the batch of environmental sensors, the method comprising: performing a plurality of electrical test sequences to the sensor inputs of the batch of environmental sensors to measure electrical responses of the sensor outputs of the batch of environmental sensors; correlating the measured electrical responses from the batch of environmental sensors to predetermined environmental parametric ranges of at least one environmental sensor so as to define correlated electrical test limits; and determining the fitness for purpose of the batch of environmental sensors if the measured electrical responses are within the correlated electrical test limits.

The predetermined environmental parametric ranges are determined by performing a plurality of tests of the at least one sensor under an environmental condition. Here the at least one sensor may form part of the batch of the sensors, but the at least one sensor may not correspond to all the sensors of the batch. The at least one sensor on which the environmental test is performed may comprise a plurality of sensors which may be completely separate from the batch of sensors. After performing the environmental test sequences to the at least one sensor the electrical test sequences are then run for the same sensors. The electrical test limits are then set based on the results of the electrical test sequences on the sensors which were also used to perform environmental tests (for example, under a gas). This correlation procedure may be performed in reverse sequence, i.e. perform the electrical tests first and then the environmental tests.

Embodiments of the present invention enable the performance of the electrical tests on a mass producible batch of sensors without requiring testing them under an environmental condition, such as under a gas, a humidity level or a pressure level. The correlated electrical test limits are achieved from a standard environmental test performed on a certain number of sensors (but not to all the batches of sensors ready for shipment) and then only the electrical test results are compared with the correlated electrical test limits. Performing only electrical tests on the environmental sensors are advantageous because it is fast, cost effective and efficient.

The testing of the environmental sensors to determine the fitness for purpose may be performed by exclusively applying electrical impulses to the each sensor of the batch of environmental sensors and by exclusively measuring electrical responses of the batch of environmental sensors.

The batch of environmental sensors may not be directly tested under an environmental condition. As mentioned before, it is only certain number of sensors, for example from a batch or sample of batches, that are tested both environmentally and electrically to determine the correlated electrical test limits.

The step of performing the plurality of electrical test sequences may be performed by an automated test equipment and the electrical responses are measured by the automated test equipment.

The electrical responses may provide calibration values that are stored within the environmental sensors.

The environmental sensors may comprise gas sensors. Each gas sensor may comprise: a dielectric membrane formed on a semiconductor substrate comprising an etched portion; a heater formed in the dielectric membrane; gas sensing electrodes formed on the dielectric membrane and a gas sensitive layer formed on the gas sensing electrodes.

The electrical impulses may be applied to the heater of each gas sensor and the electrical response may be measured across the heater and across the gas sensing electrode of each gas sensor.

The predetermined parametric ranges may be determined by running a test in the presence of a gas.

The predetermined parametric ranges may be determined from the sensor resistance variation in air and the sensor resistance variation in the gas to define the correlated electrical test limits.

The measured electrical responses from the batch of gas sensors may be compared with the correlated electrical test limits.

The fitness for purpose of the gas sensors may be determined when the measured electrical responses from the batch of gas sensors are within said correlated electrical test limits.

The gas sensors may be metal oxide gas sensors.

The environmental sensors may comprise humidity sensors. Alternatively, the environmental sensors may comprise pressure sensors.

The batch of sensors may be tested in wafer form or any other form prior to packaging.

The batch of sensors may be tested in wafer level package format.

The batch of sensors may be tested in a package strip format.

The package strip may be supported face down on a dicing tape which is further supported by a film frame.

The package strip may comprise a plurality of environmental sensors which are electrically isolated from one another.

The plurality of environmental sensors may be electrically isolated by using a conductor etching process such as an etch back process.

The plurality of environmental sensors may be electrically isolated by using of a sawing process.

The sawing process may only cut through the metal conductors between environmental sensors and keeps the integrity of the strip intact.

The sawing process may cut through the full package structure including the metal conductors between sensors to leave an array of separate sensors.

According to a further aspect of the present invention, there is provided an environmental sensor test system to determine the fitness for purpose of a batch of environmental sensors, the comprising: said batch of environmental sensors; an automated test equipment to perform a plurality of electrical test sequences to the sensor inputs of the batch of environmental sensors and to measure electrical responses of the sensor outputs of the batch of environmental sensors; a data analysis tool to correlate the measured electrical responses from the batch of environmental sensors to predetermined environmental parametric ranges of at least one environmental sensor so as to define correlated electrical test limits; and wherein the data analysis tool is configured to determine the fitness for purpose of the batch of environmental sensors if the measured electrical responses are within the correlated electrical test limits. Here the data analysis tool may be a spreadsheet application, for example MS Excel, or may be a purpose built software tool, for example Galaxy Examinator Pro.

A test system may further comprise an environmental test equipment which is configured to determine the predetermined environmental parametric ranges by performance of a plurality of tests of the at least one sensor under an environmental condition.

The environmental sensors may each store calibration values of the electrical responses.

The environmental sensors may comprise gas sensors.

Each gas sensor may comprise:
a dielectric membrane formed on a semiconductor substrate comprising an etched portion;
a heater formed in the dielectric membrane; gas sensing electrodes formed on the dielectric membrane and a gas sensitive layer formed on the gas sensing electrodes.

The automated test equipment may be configured to apply electrical impulses to the heater of each gas sensor and to measure the electrical response of the heater and across the gas sensing electrodes of each gas sensor.

A test system may further comprise a gas testing equipment which is configured to determine predetermined parametric ranges by running a test in the presence of a gas.

The gas testing equipment may be configured to determine the predetermined parametric ranges from the sensor resistance variation in air and the sensor resistance variation in the gas to define said correlated electrical test limits.

The gas sensors may be metal oxide gas sensors. Alternatively the environmental sensors may comprise humidity sensors. Alternatively the environmental sensors may comprise pressure sensors.

The batch of sensors may be tested in wafer form or any other form prior to packaging.

The batch of sensors may be tested in wafer level package format.

The batch of sensors may be packaged in a package strip format.

A test system may further comprise a film frame and a dicing tape which is supported by the film frame, wherein the package strip is supported face down on the dicing tape.

The package strip may comprise a plurality of environmental sensors which are electrically isolated from one another.

The plurality of environmental sensors may be electrically isolated by using a conductor etching technique such as an etching back technique.

The plurality of environmental sensors may be electrically isolated by using of a sawing technique.

The environmental sensors may be configured such that the sawing technique only cuts through the metal conductors between the environmental sensors and keeps the integrity of the strip intact.

The environmental sensors may be configured such that the sawing technique cuts through the full package structure including the metal conductors between sensors to leave an array of separate sensors.

A test system may further comprise a film frame prober to test the sensors.

BRIEF DESCRIPTION OF THE PREFERRED EMBODIMENTS

Some preferred embodiments of the invention will now be described by way of example only and with reference to the accompanying drawings, in which.

DETAILED DESCRIPTION OF THE PREFERRED EMBODIMENTS

Embodiments of the invention provide a method for screening gas sensors for their suitability to perform in the end application (or fitness for purpose) by means of applying electrical impulses and measuring the sensors electrical responses. Embodiments of this invention makes use of standard semiconductor production automatic test equipment (ATE) to perform electrical test sequences, the results of which are correlated to gas test performance so can be used to screen good units from reject units.

Figure 1:
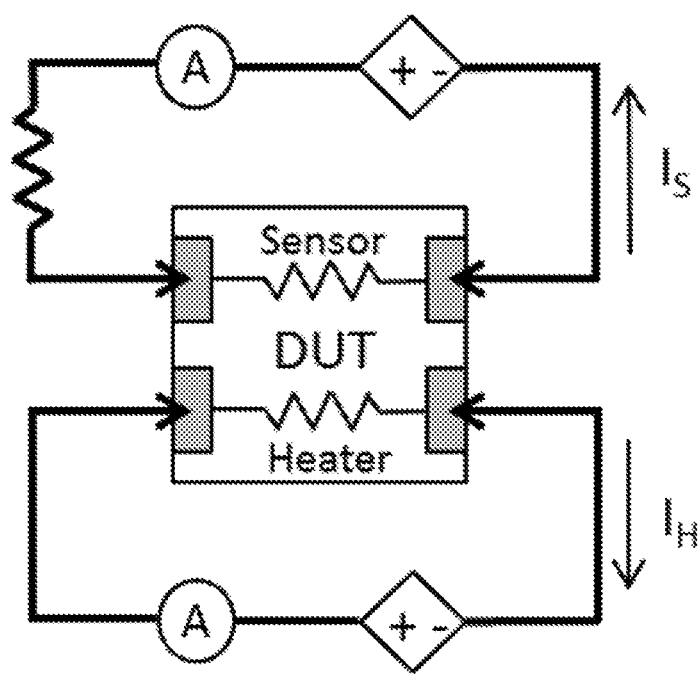
FIG. 1 illustrates an electrical test system for an environmental sensor such as a metal oxide (MOX) gas sensor.

FIG. 1 illustrates an electrical test system for an environmental sensor such as a metal oxide (MOX) gas sensor. The sensor includes a heater across which electrical impulses are applied to generate the heat. The heater can be an IR emitter which emits IR radiation to the sensor electrode on which MOX is deposited. Electrical responses (or resistances) are then measured across sensor outputs (or across sensor electrodes). Electrical responses from the sensor output are then correlated with the separate gas testing results.

The following are examples of electrical test sequences that could be used to screen gas sensors. These can be used as standalone tests, in combination with each other or with alternative test solutions not listed here since an exhaustive list is not practical. Furthermore, the results from these tests can be used to store calibration values within the sensor product under test, e.g. in one time programmable (OTP) or flash within a digital control device (not shown).

EXAMPLE 1

Apply low voltage (eg 500 mV) to heater and measure heater current and sensor resistance (R1)
Apply higher voltage (eg 1.2V) to heater and measure heater current and sensor resistance (R2)
Calculate the ratio or difference of R1 and R2 and apply test limits to all results

EXAMPLE 2

Apply voltage (eg 1V) to heater and measure heater current and sensor resistance after a delay (eg 100 ms) (R1)
Continue to apply same voltage and measure heater current and sensor resistance after a further delay (eg 1 s) (R2)
Calculate the ratio or difference of R1 and R2 and apply test limits to all results

EXAMPLE 3

Apply a sinusoidal voltage (eg from 0.8V to 1.2V at a frequency of 200 Hz) to heater for a fixed duration (eg 5 s) and measure the heater current and the resistance response of the sensor
Apply phase shift, amplitude and jitter test limits to the resulting resistance profile

EXAMPLE 4

Apply multiple voltages to the heater and measure the heater current and the sensor resistance in each case (eg 0V, 0.5V, 0V, 1.0V, 0V, 1.4V, 0V, 1.8V, 0V, 1.4V, 0V, 1.0V, 0V, 0.5V, 0V)
Calculate resistance ratios or differences and apply test limits to all results

EXAMPLE 5

Apply low voltage (eg 500 mV) to heater, sweep voltage on sensor (eg 1V to 5V) and measure heater current and sensor current at each voltage step
Apply high voltage (eg 1.4V) to heater, sweep voltage on sensor (eg 1V to 5V) and measure heater current and sensor current at each voltage step
Calculate sensor resistances and apply test limits to all values as well as ratios and differences.

As mentioned above, one or more of the above electrical tests can be applied to a plurality of batches of sensors to determine the fitness for purpose of the sensors. The fitness for purpose is determined for a large batch of production line sensors by using some or all of the electrical test sequences described above and, potentially, other electrical tests. Therefore the list of electrical tests above is not exhaustive as other electrical tests are also possible.

Figure 2:
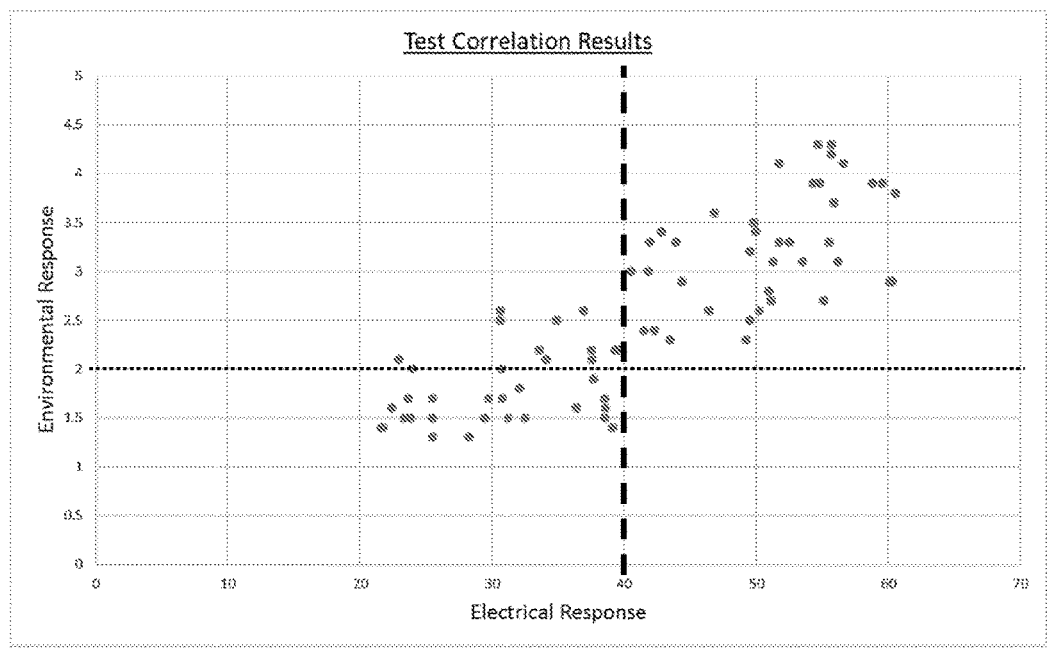
FIG. 2 illustrates correlation test results according to one embodiment of the present invention.

FIG. 2 illustrates correlation test results according to the embodiments of the present invention. The correlation test results of FIG. 2 are directed to a batch of environmental sensors such as gas sensors. Each sensor from the batch has gone through both the electrical test and environmental (gas) test separately. The 'X' axis represents the electrical test response and the 'Y' axis represents the gas test response for the same sensors of the batch of sensors. Each filled grey circle of FIG. 2 represents the correlated electrical and gas test result of each sensor of the batch of sensors. In this example, the environmental response lower specification limit (or predetermined environmental parametric range) is set to at least 2 (dotted line). Then, the electrical response lower specification limit (or correlated electrical test limit) is set, in this example, to at least 40 (dashed line) to ensure all sensors have an environmental response ≥2. It can be seen from this example data that all sensors which have an electrical response greater or equal to 40 also have an environmental response greater or equal to 2. Therefore, a lower electrical test limit of 40, in this case, guarantees the sensor will also have an environmental response of greater or equal to 2. Therefore, it is no longer necessary to perform an environmental test on further sensor batches since the electrical test is sufficient to guarantee environmental performance by applying the lower specification limit of 40 to the electrical test result. This data is given by way of example only as these limits apply to this set of data for these particular tests and this particular sensor type. Other environmental tests and/or electrical test will most likely result in different limits for those tests.

In the correlation test results of FIG. 2, the top right quadrant includes sensors which fulfil the fitness for purpose requirement. For any further batches of sensors which will be mass produced for shipment will only go through the electrical test sequences without any gas or environmental test sequences. From these further batches of sensors, those sensors achieve electrical test response above the electrical response lower specification limit, e.g. ≥40, would be marked as passing the fitness for purpose test. There is no need to do the gas test result for each sensor anymore, because it is already understood from the correlation test results of FIG. 2 that the environmental response lower specification limit is already ≥2 for those sensors which have achieved electrical response lower specification limit of ≥40. Advantageously this enables to reduce the requirement of performing an environmental test sequence on each gas sensor in a very large batch of mass producible sensors.

Figure 3:
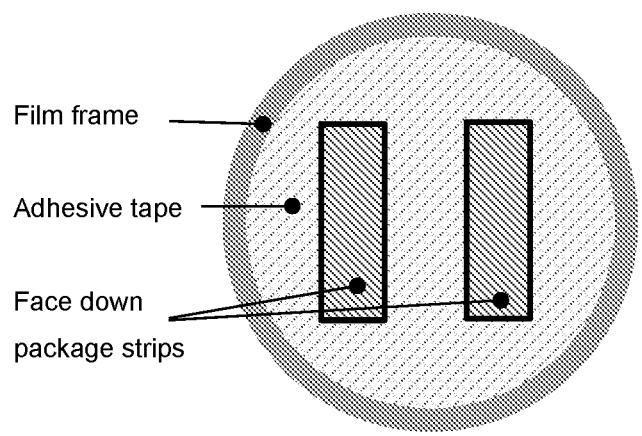
FIG. 3 illustrates a top view of a wafer film frame in which package strips of sensors are provided.

Furthermore, embodiments of the invention can include the use of wafer film frame handling formats to further reduce cost and increase throughput. FIG. 3 illustrates a top view of a wafer film frame in which package strips of sensors are provided. The package strips are face down onto a dicing adhesive tape attached to a standard dicing film frame. If the packages are electrically isolated, e.g. by use of an etch back substrate, then they can proceed straight to test. In FIG. 3, each strip is made up of a plurality of gas sensors which are at least electrically isolated from one another.

Figure 4A:
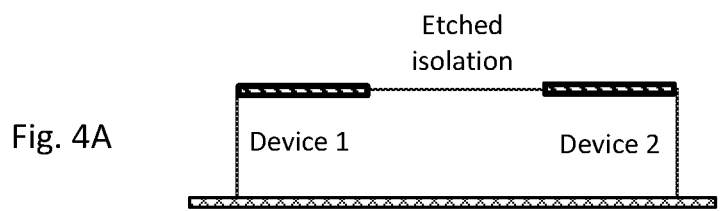
FIG. 4A to FIG. 4C illustrate exemplary electrical isolation techniques according to the embodiments of the present invention.
Figure 4B:
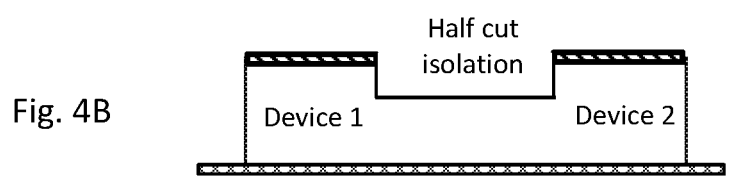
Figure 4C:
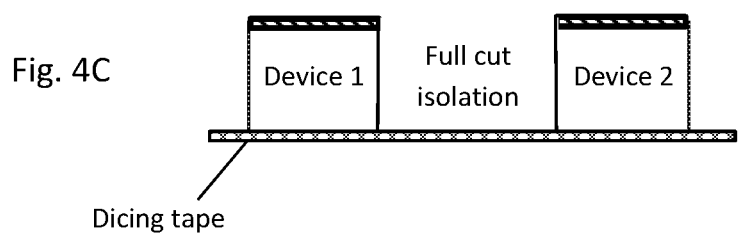

FIG. 4A to FIG. 4C illustrate exemplary electrical isolation techniques according to embodiments of the present invention. In FIG. 4A, the individual packages are electrically isolated by etching of the conductors. In order to provide isolation between packages, in FIG. 4B, the strips are half cut, i.e. sawn through the conductors of the substrate or lead-frame only to isolate devices. In FIG. 4C, the strips are full cut, i.e. sawn all the way through the substrate or lead-frame to fully singulate or isolate the devices. Once devices are electrically isolated they can be tested using a film frame prober such for example a Accretech FP3000, and a standard ATE such as a Teradyne J750.

In two embodiments, the plurality of gas sensors may be electrically isolated by using of a sawing process. The sawing process will only cut through the metal conductors between gas sensors whilst leaving the integrity of the strip intact. The sawing process may cut through the full package structure including the metal conductors between gas sensors to leave an array of singulated gas sensors.

Although the invention has been described in terms of preferred embodiments as set forth above, it should be understood that these embodiments are illustrative only and that the claims are not limited to those embodiments. Those skilled in the art will be able to make modifications and alternatives in view of the disclosure which are contemplated as falling within the scope of the appended claims. Each feature disclosed or illustrated in the present specification may be incorporated in the invention, whether alone or in any appropriate combination with any other feature disclosed or illustrated herein.

The invention claimed is:

1. A method for testing a batch of environmental sensors to determine the fitness for purpose of the batch of environmental sensors, the method comprising:
   determining environmental parametric ranges by performing a plurality of environmental tests on at least one environmental sensor under a specified environmental condition;
   performing a plurality of electrical test sequences to the sensor inputs of the at least one environmental sensor to measure electrical responses of the sensor outputs of the at least one environmental sensor;
   correlating the measured electrical responses from the at least one environmental sensor to predetermined environmental parametric ranges of the at least one environmental sensor so as to define correlated electrical test limits;
   testing the batch of environmental sensors by exclusively applying electrical impulses to each sensor of the batch of environmental sensors and by exclusively measuring electrical responses of the batch of environmental sensors; and
   determining the fitness for purpose of the batch of environmental sensors if the measured electrical responses of the batch of environmental sensors are within the correlated electrical test limits.

2. A method according to claim 1, wherein the step of performing the plurality of electrical test sequences is performed by an automated test equipment and the electrical responses are measured by the automated test equipment.

3. A method according to claim 1, wherein the electrical responses provide calibration values that are stored within the environmental sensors.

4. A method according to claim 1, wherein the environmental sensors comprise gas sensors.

5. A method according to claim 4, wherein each gas sensor comprises:
   a dielectric membrane formed on a semiconductor substrate comprising an etched portion;
   a heater formed in the dielectric membrane;
   gas sensing electrodes formed on the dielectric membrane; and a gas sensitive layer formed on the gas sensing electrodes.

6. A method according to claim 5, wherein electrical impulses are applied to the heater of each gas sensor and the electrical response is measured across the gas sensing electrodes of each gas sensor.

7. A method according to claim 4, wherein the predetermined parametric ranges are determined by running a test in the presence of a gas.

8. A method according to claim 7, wherein the predetermined parametric ranges are determined from the sensor resistance variation in air and the sensor resistance variation in the gas to define said correlated electrical test limits.

9. A method according to claim 8, wherein the measured electrical responses from the batch of gas sensors are compared with said correlated electrical test limits.

10. A method according to claim 9, wherein the fitness for purpose of the gas sensors is determined when the measured electrical responses from the batch of gas sensors are within said correlated electrical test limits.

11. A method according to claim 4, wherein the gas sensors are metal oxide gas sensors.

12. A method according to claim 1, wherein the environmental sensors comprise humidity sensors.

13. A method according to claim 1, wherein the environmental sensors comprise pressure sensors.

14. A method according to claim 1 wherein the batch of sensors are tested in wafer form or any other form prior to packaging.

15. A method according to claim 1 wherein the batch of sensors are tested in wafer level package format.

16. A method according to claim 1 wherein the batch of sensors are tested in a package strip format.

17. A method according to claim 16 wherein the package strip is supported face down on a dicing tape which is further supported by a film frame.

18. A method according to claim 16, wherein the package strip comprises a plurality of environmental sensors which are electrically isolated from one another.

19. A method according to claim 16, wherein the plurality of environmental sensors are electrically isolated by using a conductor etching process such as an etch back process.

20. A method according to claim 16, wherein the plurality of environmental sensors are electrically isolated by using of a sawing process.

21. A method according to claim 20, wherein the sawing process only cuts through the metal conductors between environmental sensors and keeps the integrity of the strip intact.

22. A method according to claim 20, wherein the sawing process cuts through the full package structure including the metal conductors between sensors to leave an array of separate sensors.

23. An environmental sensor test system to determine the fitness for purpose of a batch of environmental sensors, the test system comprising:
   said batch of environmental sensors;
   an automated test equipment to perform a plurality of electrical test sequences to sensor inputs of at least one environmental sensor and to measure electrical responses of sensor outputs of the at least one environmental sensor;
   an environmental test equipment which is configured to determine environmental parametric ranges by performing a plurality of tests on the at least one environmental sensor under a specified environmental condition;
   a data analysis tool to correlate the measured electrical responses from the at least one environmental sensor to predetermined environmental parametric ranges of the at least one environmental sensor so as to define correlated electrical test limits; and
   wherein the testing of the environmental sensors to determine the fitness for purpose is performed by exclusively applying electrical impulses to each sensor of the batch of environmental sensors and by exclusively measuring electrical responses of the batch of environmental sensors; and wherein the data analysis tool is configured to determine the fitness for purpose of the batch of environmental sensors if the measured electrical responses are within the correlated electrical test limits.

24. A test system according to claim 23, wherein the environmental sensors comprise gas sensors.

25. A test system according to claim 24, wherein each gas sensor comprises:
a dielectric membrane formed on a semiconductor substrate comprising an etched portion;
a heater formed in the dielectric membrane;
gas sensing electrodes formed on the dielectric membrane; and
a gas sensitive layer formed on the gas sensing electrodes.

26. A test system according to claim 25, wherein said automated test equipment is configured to apply electrical impulses to the heater of each gas sensor and to measure the electrical response across the gas sensing electrodes of each gas sensor.

27. A test system according to claim 25, further comprising a gas testing equipment which is configured to determine predetermined parametric ranges by running a test in the presence of a gas.

28. A test system according to claim 27, wherein the gas testing equipment is configured to determine the predetermined parametric ranges from the sensor resistance variation in air and the sensor resistance variation in the gas to define said correlated electrical test limits.

29. A test system according to claim 24, wherein the gas sensors are metal oxide gas sensors.

30. A test system according to claim 23, wherein the environmental sensors comprise humidity sensors.

31. A test system according to claim 23, wherein the environmental sensors comprise pressure sensors.

32. A test system according to claim 23 wherein the batch of sensors are in wafer form or any other form prior to packaging.

33. A test system according to claim 23 wherein the batch of sensors are packaged in wafer level package format.

34. A test system according to claim 23, wherein the batch of sensors are packaged in a package strip format.

35. A test system according to claim 34, further comprising a film frame and a dicing tape which is supported by the film frame, wherein the package strip is supported face down on the dicing tape.

36. A test system according to claim 35, wherein the package strip comprises a plurality of environmental sensors which are electrically isolated from one another.

37. A test system according to claim 36, wherein the plurality of environmental sensors are electrically isolated by using a conductor etching technique such as an etching back technique.

38. A test system according to claim 36, wherein the plurality of environmental sensors are electrically isolated by using of a sawing technique.

39. A test system according to claim 38, wherein the environmental sensors are configured such that the sawing technique only cuts through the metal conductors between the environmental sensors and keeps the integrity of the strip intact.

40. A test system according to claim 38, wherein the environmental sensors are configured such that the sawing technique cuts through the full package structure including the metal conductors between sensors to leave an array of separate sensors.

* * * * *